United States Patent [19]

Taki et al.

[11] Patent Number: 5,856,549
[45] Date of Patent: Jan. 5, 1999

[54] SILANE COMPOUND AND PROCESS FOR THE PREPARATION THEREOF

[75] Inventors: Takayuki Taki, Saitama; Masashi Nakajima, Kanagawa; Kunihiko Imanishi, Saitama; Masahide Murata, Tokyo, all of Japan

[73] Assignee: Tonen Corporation, Tokyo, Japan

[21] Appl. No.: 29,268

[22] PCT Filed: Aug. 23, 1996

[86] PCT No.: PCT/JP96/02363

§ 371 Date: May 1, 1998

§ 102(e) Date: May 1, 1998

[87] PCT Pub. No.: WO97/08176

PCT Pub. Date: Mar. 6, 1997

[30] Foreign Application Priority Data

Aug. 24, 1995 [JP] Japan ................................. 7-239247

[51] Int. Cl.$^6$ .......................................................... C07F 7/18
[52] U.S. Cl. ............................................. 556/482; 556/471
[58] Field of Search ...................................... 556/482, 471

[56] References Cited

U.S. PATENT DOCUMENTS

| 5,248,803 | 9/1993 | Aoki et al. | 556/482 |
| 5,451,693 | 9/1995 | Kubota et al. | 556/482 |

*Primary Examiner*—Paul F. Shaver
*Attorney, Agent, or Firm*—William H. Dippert; Cowan, Liebowitz & Latman, P.C.

[57] ABSTRACT

There is provided a novel silane compound, di-sec-butoxy-n-propyl methoxysilane. The aforesaid silane compound is prepared by reacting n-propyl trihalosilane with sec-butanol and then reacting a resultant reaction product with methanol.

2 Claims, 2 Drawing Sheets

SILANE COMPOUND AND PROCESS FOR THE PREPARATION THEREOF

FIELD OF THE INVENTION

The present invention relates to a novel silane compound and a process for the preparation thereof, more specifically a novel silane compound which is suitable as a catalytic component for polymerization of propylene, or as a silane coupling agent, and a process for the preparation of the same.

BACKGROUND OF THE INVENTION

It is known that a polymer with high stereoregularity can be prepared by the use of alkoxy silanes as a catalytic component in the polymerization of propylene. However, it was impossible to sufficiently attain both high polymerization activity and high stereoregularity with known alkoxy silanes as a catalytic component in the polymerization of propylene.

Further, silane compounds are expected to be useful as silane coupling agents and resin modifiers. Accordingly, new silane compounds are awaited.

DISCLOSURE OF THE INVENTION

An object of the invention is to provide a novel silane compound useful as a highly active catalytic component for polymerization of propylene with high stereoregularity or as a silane coupling agent, and a process for the preparation of the same.

The present invention provides a silane compound represented by the following formula (I):

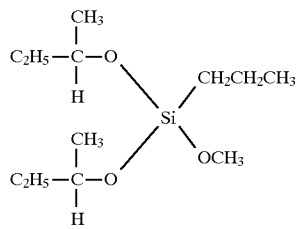

that is, di-sec-butoxy-n-propyl methoxysilane.

The present invention secondly provides a process for the preparation of the novel silane compound represented by the aforesaid formula (I). That is, the silane compound represented by the aforesaid formula (I) is prepared by reacting n-propyl trihalosilane with sec-butanol and then reacting a resultant reaction product with methanol.

BEST MODE FOR THE PRACTICE OF THE INVENTION

Figure 1:
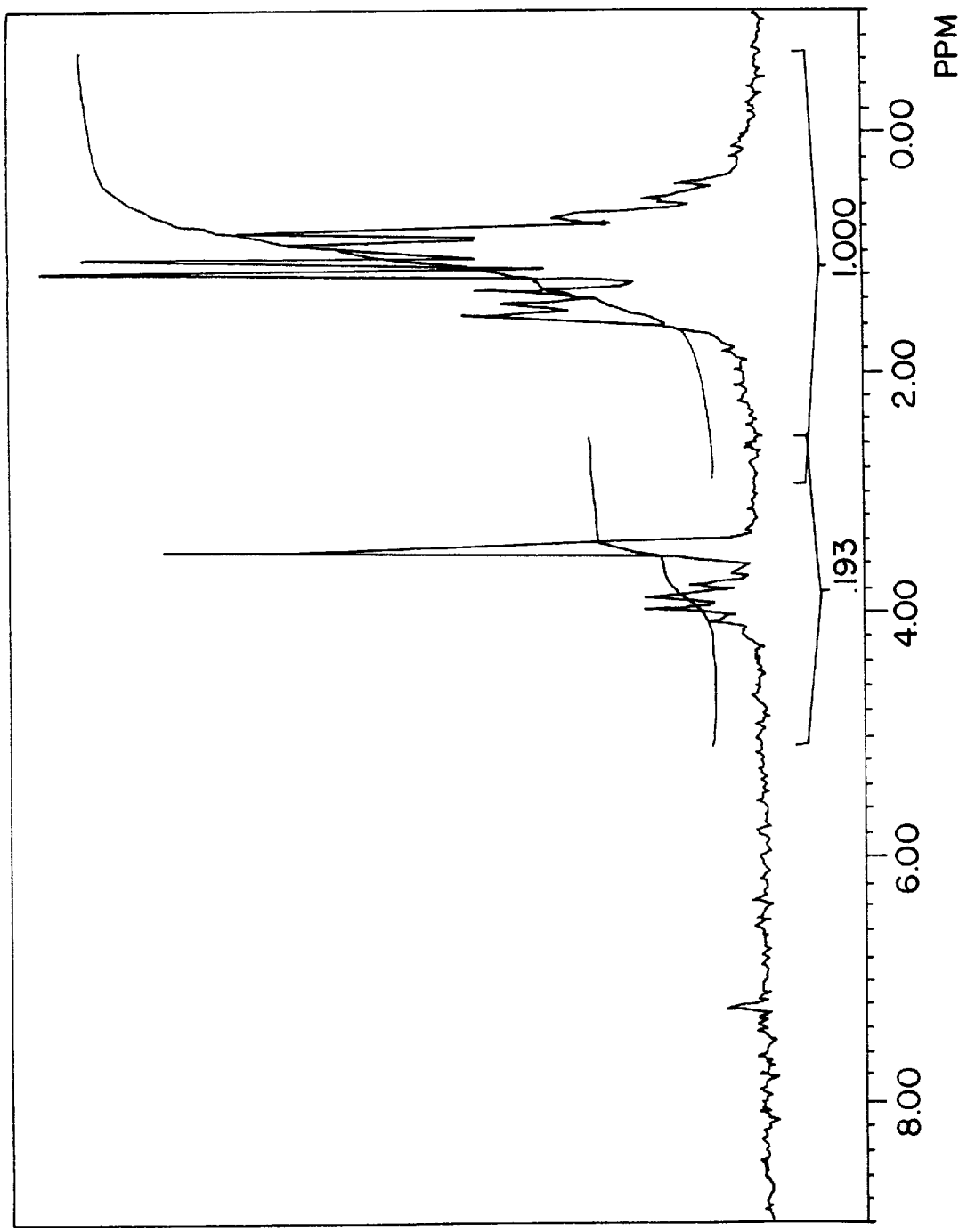
FIG. 1 is a chart of $^1$H-NMR on di-sec-butoxy-n-propyl methoxysilane prepared in Example 1. The curves above the peaks and the numbers below the peaks represent an area intensity of each peak.

This silane compound (I) has a boiling point of 125° C./0.1 mmHg. The structure of this silane compound may be confirmed by GC-MS, $^1$H-NMR, infrared absorption spectrum (IR) and so on.

When compound (I) is analyzed by $^1$H-NMR, signals are observed at δ=0.4–1.8 for the hydrogen atoms except ones bound to the carbon atoms directly bound to the oxygen atoms in the n-propyl and sec-butoxy groups, δ=3.5 for the hydrogen atoms bound to the carbon atoms in the methoxy group and δ=3.7–4.1 for the hydrogen atoms bound to the carbon atoms directly bound to the oxygen atoms in the sec-butoxy groups.

In analysis by IR spectra, a large absorption due to the SiOC bonds is observed around 1,100 cm$^{-1}$.

Olefinic polymers, such as polypropylene and polybutene, with high stereoregularity can be prepared at high polymerization activity using the silane compound (I) as a catalytic component.

As the silane compound (I) has hydrolytic groups, it can be used as a silane coupling agent, a polymerizable monomer and a resin modifier.

In the present process, n-propyl trihalosilane used as a raw material is represented by the following formula (II):

wherein X stands for a halogen atom, preferably Cl or Br. It may easily be prepared from propylene and trihalosilane (H—SiX$_3$) through hydrosilylation reaction:

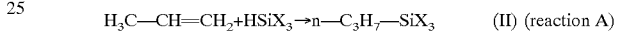

In the above reaction, 0.9 to 1.1 moles of trihalosilane is used per mole of propylene. The reaction is conducted in conditions of a temperature of 100° to 200° C. and 10 minutes to 10 hours, preferably with the use of a platinum catalyst such as chloroplatinic acid and platinum-1,1,3,3-tetramethyl-1,3-divinyldisiloxane complex. Solvents may also be used, such as benzene and toluene. N-propyl trihalosilane is commercially available. Such commercial products maybe used in the present invention.

In the present invention, the aforesaid n-propyl trihalosilane (II) is reacted with sec-butanol. Sec-butanol is known per se and is commercially available. The reaction is considered to proceed as follows:

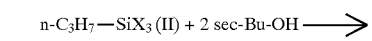

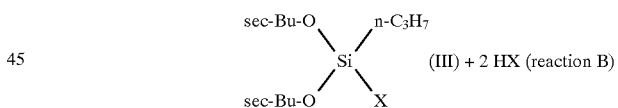

wherein sec-Bu stands for sec-butyl group, hereinafter the same. This reaction results in the formation of compound (III).

In the aforesaid reaction (B), 2 to 2.5 moles of sec-butanol maybe used per mole of n-propyl trihalosilane (II). The reaction may be carried out at a temperature of, for instance, 0° to 100° C. for 10 minutes to 5 hours, preferably at a temperature of 10° to 70° C. for 30 minutes to 4 hours. Solvents may be used, such as organic solvents, for instance, hexane, ethers, petroleum ether and benzene.

In the invention, it is preferred to use a hydrogen halide acceptor in the reaction mixture in order to facilitate the reaction. Examples of the hydrogen halide acceptor include tertiary amines such as triethyl amine, and nitrogen-containing heterocyclic compounds such as pyridine, quinoline and isoquinoline with pyridine and quinoline being preferred. It is preferred that the hydrogen halide acceptor is used in an amount of 2 to 2.5 moles per mole of n-propyl trihalosilane.

In the present invention, compound (III) is then reacted with methanol to prepare the silane compound (I) of the invention as follows:

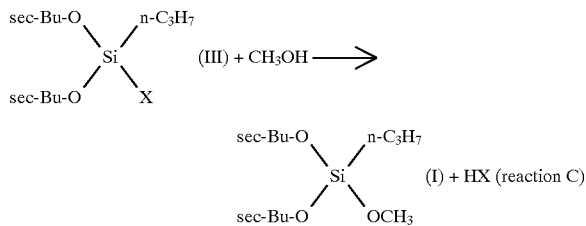

In the above reaction, 1 to 2 moles of methanol may be used per mole of compound (III). The reaction may be carried out at a temperature of 0° to 100° C. for 10 minutes to 5 hours, preferably a temperature of 10° to 70° C. for 30 minutes to 2 hours. It is preferred to use a hydrogen halide acceptor also in reaction C in order to facilitate the reaction. The hydrogen halide acceptors mentioned for reaction B maybe used also here. A hydrogen halide acceptor used here may be the same as or different from one used in preceding reaction, but is generally the same as that. It is preferred to use 1 to 2 moles of the hydrogen halide acceptor per mole of compound (III).

In the aforesaid reactions B and C, inert gas may be blown in to remove the formed hydrogen halide from the reaction system so as to facilitate the reactions.

The novel silane compound (I) maybe prepared at high yield in the aforesaid preparation process.

EXAMPLES

The invention will further be explained with reference to the following Examples.

Example 1

In a 500 ml three-neck flask provided with a magnetic stirrer, a reflux condenser and a dropping funnel were charged 15.7 g (0.0887 mole) of n-propyl trichlorosilane as a commercial product and 300 ml of hexane, to which a mixture of 13.9 g (0.176 mole) of pyridine and 13.1 g (0.177 mole) of sec-butanol was added dropwise over a period of 90 minutes at room temperature under stirring.

After refluxing for further 4 hours, 5.5 g (0.17 mole) of methanol and 6.8 g (0.086 mole) of pyridine were added and refluxing was continued for further 2 hours and then the reaction was ended.

Figure 2:
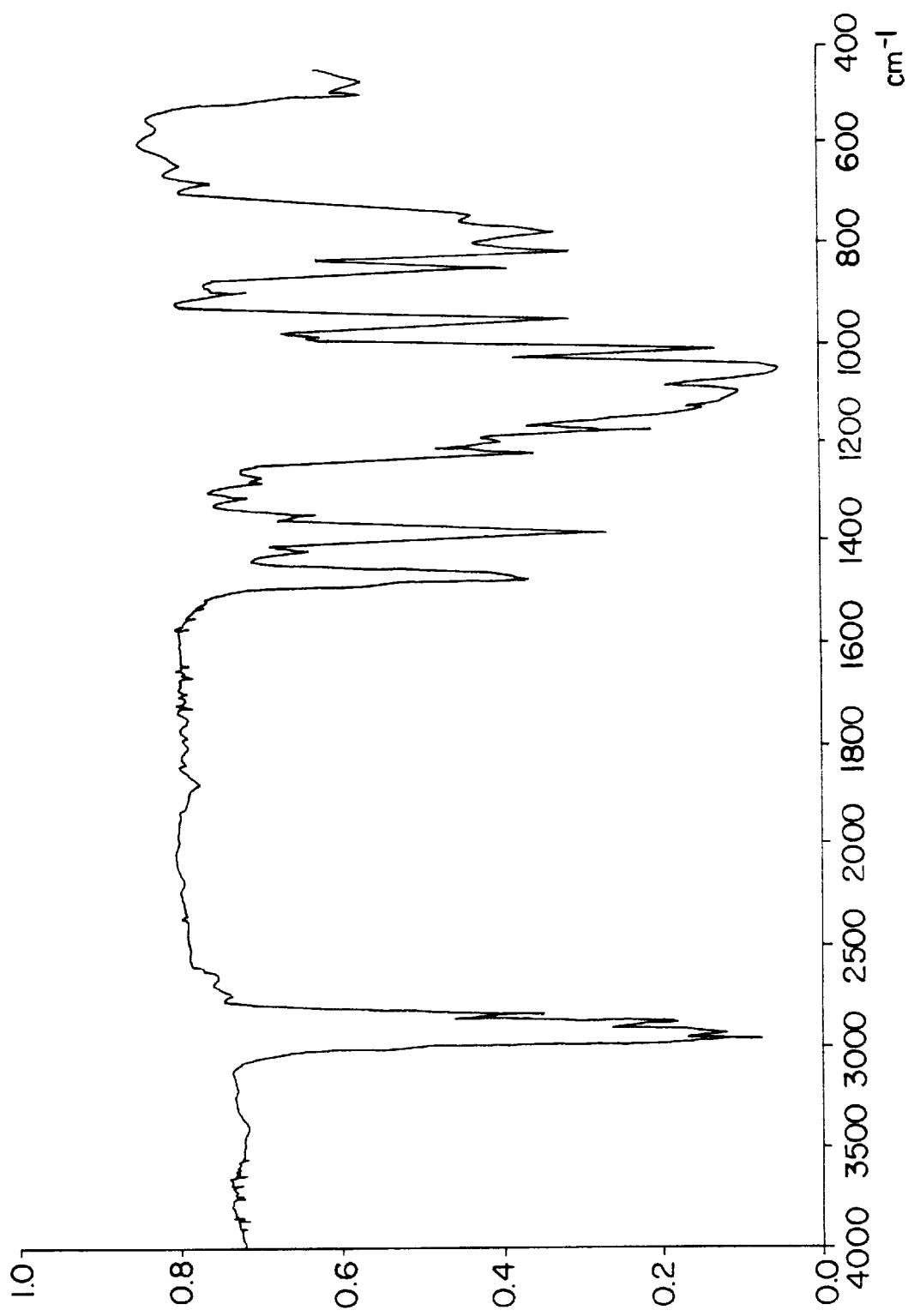
FIG. 2 is a chart of IR on di-sec-butoxy-n-propyl methoxysilane prepared in Example 1.

After the salt formed was filtered off and hexane was distilled off, a liquid of 6.8 g (0.027 mole) with a boiling point of 125° C./0.1 mmHg was obtained by vacuum distillation. This product was confirmed to be di-sec-butoxy-n-propyl methoxysilane by GC-MS, $^1$H-NMR and IR. FIGS. 1 and 2 are the charts of $^1$H-NMR and IR, respectively. The yield was 30%.

The $^1$H-NMR and IR measurements were conducted in the following conditions.

$^1$H-NMR Unit: HITACHI R-1500 (Hitachi Seisakusho); Solvent: $CD_3Cl$; Standard reference material: remaining chloroform; IR Unit: 1600 Series FT-IR (Perkin Elmer); Method: liquid film method (KBr plate). HP 5970 B (Hewlett-Packard) was used for GC-MS. The GC-MS measurement results: values of m/e (spectral intensity ratio) are as follows: 248(0.34), 233(12.21), 219(100), 205(27.52), 177(19.72), 175(25.24), 149(23.59), 147(27.01), 119 (50.63), 93(49.14) and 77(50.49).

INDUSTRIAL APPLICABILITY

The present invention provides a novel silane compound which is useful as a catalytic component for polymerization of propylene, or as a silane coupling agent, and a process for the preparation of the same.

What is claimed is:

1. A silane compound represented by the following formula (I):

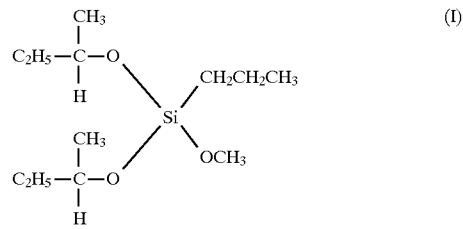

2. A process for the preparation of the silane compound claimed in claim 1, characterized in that n-propyl trihalosilane is reacted with sec-butanol and then a resultant reaction product is reacted with methanol.

* * * * *